United States Patent [19]

Lichtenstein

[11] 4,448,204
[45] May 15, 1984

[54] LIQUID CRYSTAL INFILTRATION SENSING SYSTEM

[75] Inventor: Joseph Lichtenstein, Colonia, N.J.

[73] Assignee: Whitman Medical Corporation, Clark, N.Y.

[21] Appl. No.: 423,205

[22] Filed: Sep. 24, 1982

Related U.S. Application Data

[62] Division of Ser. No. 137,741, Apr. 7, 1980, Pat. No. 4,378,808.

[51] Int. Cl.$^3$ .............................................. A61B 5/00
[52] U.S. Cl. .................................. 128/736; 374/162; 116/216
[58] Field of Search .................. 128/736; 40/448; 116/206, 207, 216; 374/162

[56] References Cited

U.S. PATENT DOCUMENTS

| | | | |
|---|---|---|---|
| 3,469,448 | 9/1969 | Swengel, Sr. | 73/356 |
| 3,661,142 | 5/1972 | Flam | 128/736 |
| 3,951,133 | 4/1976 | Reese | 128/736 |
| 3,957,202 | 5/1976 | Hornsby, Jr. | 428/1 |
| 3,998,210 | 12/1976 | Nosari | 128/736 |
| 4,015,591 | 4/1977 | Suzuki et al. | 128/736 |
| 4,030,482 | 6/1977 | Navato | 128/736 X |
| 4,064,872 | 12/1977 | Caplan | 128/736 |
| 4,079,529 | 3/1978 | Jennen et al. | 428/1 |

Primary Examiner—Kyle L. Howell
Assistant Examiner—Christine A. Fukushima
Attorney, Agent, or Firm—Holman & Stern

[57] ABSTRACT

A patch of temperature-sensitive liquid crystal material adheres to a patient's skin to serve as an indicator of infiltration during intravenous (or intraarterial, intralymphatic vessel, etc.) insertion procedures. The material is selected so as to have a constant color over a temperature range which spans the normal skin temperature range. The patch is placed immediately downstream of the insertion point and preferably has a straight forward edge to permit rapid color change over a broad section of the patch in response to infiltration. The patch may include a downstream extension, remote from the likely infiltration region, which experiences infiltration-responsive color change considerably later than the forward edge, thereby providing a color contrast to facilitate visual detection. Alternatively, a portion of the patch is permanently colored to have the same color as the patch at normal skin temperatures; the permanently colored portion therefore provides color contrast when the patch color changes due to infiltration.

11 Claims, 12 Drawing Figures

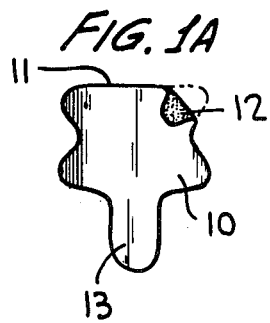
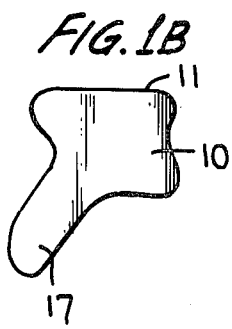
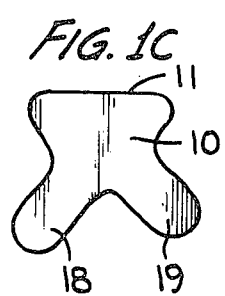
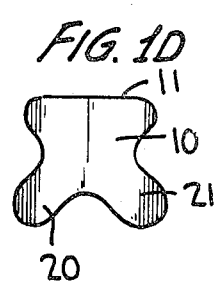
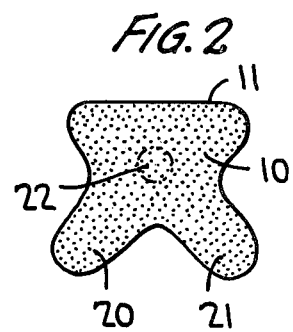
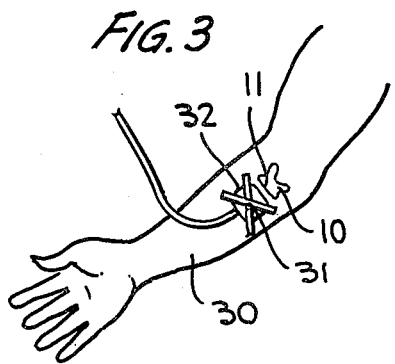
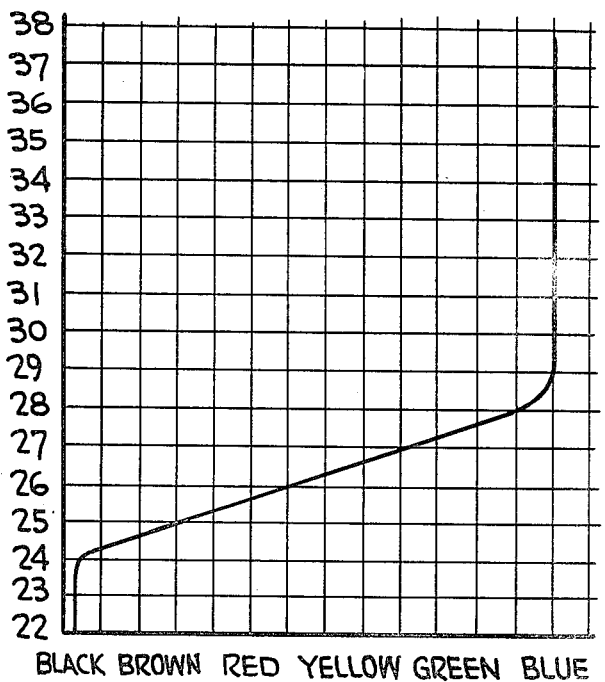
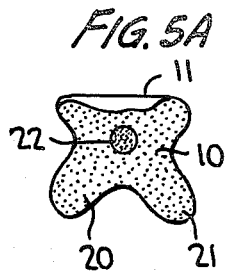
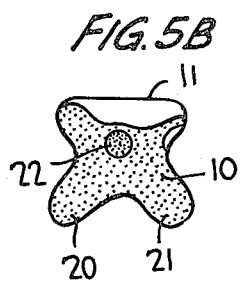
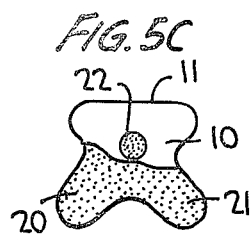
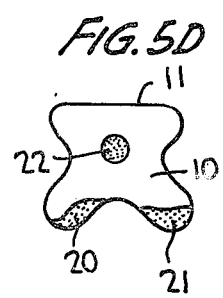

LIQUID CRYSTAL INFILTRATION SENSING SYSTEM

This is a divisional of application Ser. No. 06/137,741, filed Apr. 7, 1980 now U.S. Pat. No. 4,378,808 issued Apr. 5, 1983.

TECHNICAL FIELD

The present invention relates to sensing infiltration of fluid into a portion of a patient's body other than the intended vein, artery, lymphatic vessel, etc., during intravenous or similar fluid insertion procedures. More particularly, the present invention relates to a simplified infiltration detection apparatus and method.

BACKGROUND ART

The technique of intravenous, intra-arterial or intra-lymphatic vessel therapy by the invasion process, either for therapeutic or diagnostic purposes, is well known and standard medical procedure. A puncture into the vessel site is required to permit a needle, syringe or catheter to be inserted, thereby permitting the infusion of a fluid. When the inserted needle, syringe or catheter remains fixed in the vein, artery or lymphatic vessel, fluid entering the vessel mixes with the flow of blood and travels the path designated by the particular vessel to its tributaries. If the needle or catheter, through any inadvertent means, punctures the vessel, an egress of fluid into the surrounding tissues ensues. This egress can be caused by a number of means, including: direct puncture, wearing; degradation of the vessel wall; general fragility of the vessel wall; or chemical destruction of the wall. When this occurs, the infusing fluid is directed into the surrounding tissue cells. Such misdirection of infusion fluid during the course of therapy or diagnostic procedure is considered an "infiltration". The result can be an irritation, swelling, or inflammation of the surrounding tissues as well as the development of clots therein, all in combination or singularly developing, depending upon the amount of invasive fluid and the type of material being infused. It will be appreciated that infiltration is a painful situation and dangerous to the welfare of the patient under treatment.

Prior art infiltration detection devices depend on mechanical or electrical sensors of back pressure in the fluid delivery system. Such sensors are necessarily complex and expensive. Moreover, for safety's sake, such sensors have to be adjusted to respond in a highly sensitive manner to any back pressure condition; as a consequence, a false indication is often developed due to such occurrences as a temporary restriction or bending in the supply tube. Back pressure detection by the sensors results in an alarm sounding, which, particularly in the case of a false alarm, is an unnecessarily frightening condition for the patient.

It is therefore an object of the present invention to provide a simple and inexpensive method and apparatus for sensing infiltration whereby the aforesaid disadvantages of the prior art are eliminated.

As will be described in greater detail below, the present invention utilizes the known capability of liquid crystal material, when disposed flush against the skin, to indicate sub-cutaneous temperature changes. For example, U.S. Pat. No. 3,998,210 to Nosari (which patent is incorporated herein by reference) describes a liquid crystal strip secured to a patient's skin in order to permit visual location of a vein for a fluid infusion procedure. The films described therein, as well as the color range and chemicals described, are applicable to the present invention, the difference being that in the present invention the particular films defined by the Nosari patent are utilized for a new and unobvious purpose.

DISCLOSURES OF THE INVENTION

In accordance with the present invention, a patch of liquid crystal material is affixed to a patient's skin immediately downstream of the point of insertion of a fluid infusion. The liquid crystal material is designed to have a constant temperature over the normal range of skin temperatures for the human body. Below that range the patch changes color to signify an infiltration in the sub-cutaneous region beneath the patch. The forward end of the patch (i.e. the edge proximate the point of infusion) is preferably straight and extends transversely to the direction of flow of infusion fluid. The straight edge provides a broad frontal region which quickly changes color in response to sub-cutaneous infiltration. In addition, the patch preferably includes some means to provide a color contrast whereby a change in color due to an infiltration can be readily observed. This color contrast may be provided by a downstream extension of the patch which is relatively remote from the point of expected infiltration and therefore experiences color changes in response to the infiltration somewhat later than the forward edge of the patch. Alternatively, the contrast may be provided by a permanently colored portion of the patch, the permanent color being the same as the color of the remainder of the patch when subjected to normal skin temperature; thus, as the patch responds to an infiltration by changing color, the permanent color portion provides contrast to readily indicate that the infiltration has occurred.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings, wherein:

FIGS. 1A, 1B, 1C and 1D are respective plan views of liquid crystal patches employed in the present invention;

FIG. 2 is a plan view of a liquid crystal patch showing a contrast portion thereof for permitting rapid determination of infiltration;

FIG. 3 is a diagrammatic view indicating the positioning of the liquid crystal patch in accordance with the present invention;

FIG. 4 is a plot of temperature versus color for a typical liquid crystal patch employed in accordance with the present invention;

FIGS. 5A, 5B, 5C and 5D are plan views of a liquid crystal patch during respective progressive stages of a sensed infiltration; and FIG. 6 is a plan view of another liquid crystal patch embodiment of the present invention.

BEST MODE OF CARRYING OUT THE INVENTION

Referring specifically to FIG. 1A of the accompanying drawings, a patch 10 of liquid crystal material is illustrated. Patch 10 may be constructed in accordance with the techniques described in the aforementioned U.S. Pat. No. 3,998,210 to Nosari. Alternatively, patch 10 may be constructed in accordance with any technique whereby the strip is responsive to temperature change by changing colors. The forward edge 11 of the strip (the upper edge in FIG. 1A) is straight; the remaining edges are preferably curved with the respective corners being arcuate. The underside 12 of patch 10 is treated with an adhesive material so that underside 12 may be placed directly against the skin to secure the patch thereto. There are numerous medically-approved adhesive backings which can serve the purpose described. A suitable non-stick protective paper backing may be secured to the underside of the patch prior to its intended use, thereby avoiding the patch sticking to other patches or its package. The end of patch 10 remote from forward edge 11 includes an extension 13 which serves a purpose to be described below.

The actual peripheral configuration of patch 10 is unimportant other than the fact that forward edge 11 should be straight and the corners should be rounded, the latter feature aiding in preventing injuries that might occur to a patient because of sharp corners. Other possible configurations are shown in FIGS. 1B, 1C and 1D wherein like reference numerals designate like components in FIG. 1A. The only major distinction in FIGS. 1B, 1C and 1D relative to FIG. 1A, concerns the position of extensions 17 (FIG. 1B), 18 and 19 (FIG. 1C) and 20 and 21 (FIG. 1D). Specifically, rearward extension 17 in FIG. 1B is shown displaced from the longitudinal axis of patch 10 as compared to the on-axis extension 13 of FIG. 1A. The patch of FIG. 1C shows two extensions 18 and 19, extending rearwardly on opposite sides of the longitudinal axis of the patch. Similar though shorter extensions 20 and 21 are illustrated in FIG. 1D.

The thickness dimension (the dimension into the plane of the drawing) of patch 10 should be sufficiently small so that the patch can rapidly respond to temperature changes and adequately conform to the skin area on which it is placed. On the other hand, the film should be sufficiently thick to permit it to be used over at least a 48 hour period. I have found that a thickness between 2 and 20 mils provides the necessary strength without sacrificing flexibility or speed of temperature response.

The color range of the patch 10 is preferably as illustrated in FIG. 4. Specifically, the patch remains at a constant color for temperatures above 28° centigrade; in the most usual case, that color will be blue as indicated in FIG. 4. It is noted that this range of 28° and above includes the range of 30° centigrade to 33° centigrade which is generally considered the normal skin temperature. Below 28° color of the patch changes progressively to green, yellow, red, brown and then black as the temperature decreases.

As illustrated in FIG. 3, the pressure sensitive patch 10 is placed on the patient 30 with its straight forward edge 11 immediately downstream of the point of infusion 31 or forward of the dressing 32 which covers the site of the puncture. This positions the patch 10 immediately over or just downstream of that portion of the inserted needle or catheter lying below the skin surface in the vein, artery or lymphatic vessel. When so placed on the skin, the patch assumes the color dictated by the temperature of the skin, which in the case of the temperature range illustrated in FIG. 4 is blue.

The function of projections 13, 17, 18 and 19 in FIGS. 1A, 1B and 1C is to provide a portion of the patch remote from the forward edge 11 which experiences the temperature change due to infiltration after the forward edge. Thus, in response to an infiltration, the forward edge of the patch 10 begins to change color while the rearward edge changes color only after a considerable delay. The contrast between the two colors provides a rapid visual indication that an infiltration has occurred. As an alternative to using the projections to provide such contrast, a portion 22 (reference FIG. 2) of the patch 10 may be permanently colored to have the same color assumed by patch 10 in response to the normal skin temperature range. In the example given in the plot of FIG. 4, this color would be blue; therefore, the circular area of FIG. 2 designated by the numeral 22 would be permanently colored blue. Upon change of patch color in response to an infiltration, the blue dot 22 remains in contrast to the green, yellow, brown or black color assumed by the patch.

When an infiltration occurs, the fluid entering the patient's body through a needle or catheter escapes into the surrounding tissue. This fluid is at ambient temperature and tends to reduce the temperature of the tissue which directly influences the color of the temperature sensitive film patch 10. The color of the film patch at ambient temperature (approximately 26° centigrade) is yellow which immediately shows up on the patch. Specifically, as illustrated in FIG. 5A, the region of the patch just rearward of forward edge 11 begins to change color first. As the fluid advances into more tissue, more of the film changes as shown by the progressive color change illustrated in FIGS. 5B, 5C and 5D. It is noted, however, that the permanently colored dot 22 remains blue to provide an accurate contrast and therefore a clear indication that an infiltration has occurred. It is also noted that the projections 20 and 21 are the last portions of the patch 10 to reflect this color change, therefore also serving as a contrast indication. Because of the contrast provided by the dot 22 or by the projections 20, 21, the patient can be instructed to note color changes and request medical assistance. Thus, an advancing infiltration can be terminated before it becomes dangerous to the patient's welfare. The immediate advisement of the initiation of an infiltration can avoid serious medical complications and reduce the overall additional costs related to the treatmen of any possible problems which may be incurred.

It should be noted that the present invention is not limited to providing an adhesive backing on the underside of patch 10; that is, it is possible to employ adhesive tape over a portion of the patch, or to apply an adhesive material immediately prior to use. However, the preferred embodiment is to provide the patch with an already applied adhesive backing.

It should be noted that the contrast area 22, shown in the form of a dot in FIG. 2, can also be provided in the form of a border around the patch as shown in FIG. 6 or it may take any position or geometrical configuration on the patch. The important point, if this permanent contrast indicator is used, is that it be of the same color assumed by the patch in response to the normal skin temperature range of 30° centigrade to 33° centigrade.

It should be noted that particular color indication in FIG. 4 is not limiting and that a temperature sensitive film of any type may be employed, the only limitation being that the color of the patch be constant over the normal range of skin temperatures and that this color be different from the color assumed by the patch in response to ambient temperature normally found in hospital and clinic environments.

It should be noted that the infusion material, even though at ambient temperature, does not alter the skin temperature when flowing in a vein or artery because it mixes with the flowing blood which is at a considerably higher temperature than the skin, namely approximately 37° centigrade. Thus, the patch does not chage temperature when the infusion material is flowing properly into the vein, artery or lymphatic vessel.

The temperature sensitive patch described herein is simple and inexpensive for detecting the advance of an infiltration. The color change is readily observable and does not require professional interpretation. It can be utilized on all patients, including out-patients, with intravenous therapy, and provides a color change only in response to infiltration problems.

While I have described and illustrated various specific embodiments of my invention, it will be clear that variations of the details of the construction which are specifically illustrated and described may be resorted to without departing from the spirit and scope of the invention and defined in the appended claims.

I claim:

1. A method of detecting infiltration of infusion fluid into a patient's body tissues surrounding the point of infusion into a vessel, said method comprising the steps of:

puncturing the patient's skin with an infusion apparatus to infuse fluid into said vessel;

affixing and conforming to the skin of the patient, at a location immediately downstream of the puncture by the infusion device, a patch of material which changes in color in response to changes in skin temperature, said patch having a first color over a range of temperatures which includes 30° cent rigrade through 33° centigrade and having a second color at temperatures below that range; and observing said affixed patch for changes from said first color to said second color.

2. The method according to claim 1 wherein said patch includes a portion which permanently has said first color, and wherein said step of observing includes observing said patch for contrast in color between said portion and the remainder of the patch.

3. The method according to claim 1 wherein said first color is blue and wherein said second color changes from blue to green to yellow to red to brown, in turn, as the temperature of the patch falls from approximately 28° centigrade.

4. The method according to claim 3 wherein said patch is provided with an adhesive coating on the underside, and wherein said step of affixing includes pressing the underside of said patch against the patient's skin.

5. The method according to claim 1 wherein said patch includes a straight edge and wherein said step of affixing includes placing said straight edge proximate and immediately downstream of said puncture.

6. A method of detecting variation in temperature of a liquid from within a pre-determined continuous range of temperatures, said method comprising the steps of:

providing a patch of thin temperature-sensitive film which has a variable color versus temperature characteristic and which remains at one color when at temperatures within said pre-determined range of temperatures;

providing a prescribed area on said patch which is permanently colored at said one color;

applying said patch to a surface of a body in which said liquid is disposed below said surface; and observing the applied patch to determine if the variable color portion differs from said one color of said prescribed area.

7. The method according to claim 6 wherein the liquid in said body is blood.

8. The method according to claim 6 wherein the step of applying includes adhering said patch to said surface of said body.

9. The method according to claim 6 wherein said body is a living human body.

10. The method according to claim 6 wherein said step of providing said prescribed area includes providing that area as a border area on said patch.

11. A method of monitoring temperature change of a substance in a body at a surface of the body which is not in direct contact with the substance by adhering a patch of liquid crystal material to said surface, said liquid crystal material having a variable color versus temperature characteristic wherein the material remains at one color over a pre-determined range of temperatures and varies from that color when the temperature of the patch varies outside said pre-determined range, said method comprising the steps of:

providing a prescribed area on said patch which is permanently colored at said one color; and observing the applied patch to determine if the variable color portion differs from the color of said prescribed area.

* * * * *